(12) United States Patent
Leonard

(10) Patent No.: US 8,815,282 B1
(45) Date of Patent: Aug. 26, 2014

(54) COMMERCIAL METHOD FOR PRODUCTION OF ROOM TEMPERATURE-LIQUID CETYL MYRISTOLEATE

(76) Inventor: Edward C. Leonard, Memphis, TN (US)

( * ) Notice: Subject to any disclaimer, the term of this patent is extended or adjusted under 35 U.S.C. 154(b) by 477 days.

(21) Appl. No.: 12/615,552

(22) Filed: Nov. 10, 2009

Related U.S. Application Data

(62) Division of application No. 11/182,201, filed on Jul. 15, 2005, now abandoned.

(51) Int. Cl.
*A61K 9/48* (2006.01)
(52) U.S. Cl.
USPC .......................................................... 424/451

(58) Field of Classification Search
None
See application file for complete search history.

(56) References Cited

U.S. PATENT DOCUMENTS

| | | |
|---|---|---|
| 4,049,824 A | 9/1977 | Diehl |
| 4,113,881 A | 9/1978 | Diehl |
| 5,569,676 A * | 10/1996 | Diehl ............................ 514/549 |
| 6,713,512 B1 * | 3/2004 | Leonard ........................ 514/559 |
| 2002/0102340 A1 * | 8/2002 | McGrane et al. ............. 426/519 |

* cited by examiner

*Primary Examiner* — Snigdha Maewall

(74) *Attorney, Agent, or Firm* — Wyatt, Tarrant & Combs, LLP; William S. Parks

(57) ABSTRACT

This invention provides a commercially feasible method to produce ambient-temperature-liquid cetyl myristoleate in commercial quantities. In addition, the invention relates to the use and benefits of the ambient-temperature-liquid CMO product made by this commercial method.

17 Claims, 1 Drawing Sheet

The Reaction of Cetyl Alcohol with Myristoleic Acid to Yield Cetyl Myristoleate
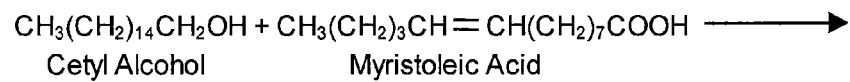
Cetyl Alcohol      Myristoleic Acid
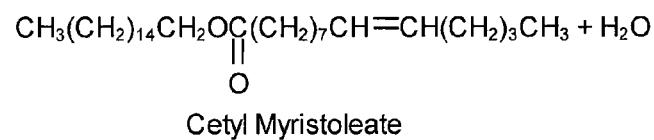
Cetyl Myristoleate

COMMERCIAL METHOD FOR PRODUCTION OF ROOM TEMPERATURE-LIQUID CETYL MYRISTOLEATE

CROSS-REFERENCE TO RELATED APPLICATIONS

This is a divisional filing from U.S. patent application Ser. No. 11/182,201, filed on Jul. 15, 2005, pending. Such parent application is referenced in full within this filing.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to cetyl myristoleate (CMO). More particularly, the present invention relates to a commercial method for producing ambient-temperature-liquid cetyl myristoleate. The present invention further relates to the use and benefits of the ambient-temperature-liquid CMO product made by this commercial method.

2. General Background of the Invention

Cetyl myristoleate (CMO) is the ester produced by the reaction of cis-9-tetradecenoic acid (myristoleic acid) with 1-hexadecanol (cetyl alcohol). CMO was originally isolated as a natural product from a National Institutes of Health (NIH) albino mouse strain that was resistant was shown to have considerable anti-arthritic properties. Synthesized CMO demonstrated a similar protective effect. In the peer-reviewed journal *Pharmacological Research*, Hunter et. al show that in mice, pure CMO causes a significant reduction in the incidence and severity of arthritis (2). Furthermore, U.S. Pat. Nos. 4,049,824, 4,113,881, and 5,569,676 issued to Diehl relate to the use of CMO as an alleviator of arthritis (3, 4, 5).

Beginning in the early 1990s nutraceuticals containing CMO have been widely used for pain and inflammation relief in osteoarthritis. These CMO-containing nutraceuticals appear to be gaining market share perhaps partly as a result of comparison with some adverse physiological effects of the Cox-2 inhibitors such as Vioxx®, Bextra® and Celebrex® (registered trademarks of: Merck & Co., Whitehouse Station, N.J.; Pharmacia & Upjohn Company, North Peapack, N.J.; and G.D. Searle & Co., North Peapack, N.J., sold by prescription.)

Softgels (soft gelatin capsules) are becoming popular dosage forms for the administration of liquids, suspensions, pastes and dry powders in the dietary supplement industry. There are many dietary supplements in the softgel formulation. For example, GNC sells the vitamin supplement GNC A-Z in softgel capsule form, Nature Made provides, among others, Flaxseed oil, Conjugated Linoleic Acid (CLA), and Evening Primrose Oil in softgel formulations, and Nature's Bounty provides a Vitamin E supplement in softgel form. Softgels are not limited to dietary supplements. Pain relief, antiviral, laxative and many other medications can also be made or formulated into softgel capsules. Softgels have distinct advantages including, but not limited to; 1) ease of swallowing, 2) the ability to mask unpleasant odors and tastes, 3) the ability to have an elegant appearance with a wide choice of colors, 4) are easily dissolved in the digestive tract, and 5) have the possibility of enhanced bio-availability of the active ingredient.

Up to now, commercially available CMO has been made by the esterification of mixed fatty acids with cetyl alcohol. This has been done commercially in multi-ton quantities. Commercial cetyl esters of mixed myristic/myristoleic acids comprise a hard wax with a melting point of about 48° C. (~120° F.). Unfortunately, this material cannot be injected directly into softgel capsules. Ambient-temperature liquid CMO has been made by Dr. Diehl in his work on the effect of CMO on arthritis in mice. However, in this work, CMO was synthesized by the esterification of highly pure myristoleic acid with cetyl alcohol. The projected cost of using such highly purified myristoleic acid to yield commercial quantities of ambient-temperature liquid CMO is prohibitive. For example, Dr. Diehl's work on the effect of CMO on arthritis in mice (1) synthesized cetyl myristoleate by the esterification of highly pure myristoleic acid with cetyl alcohol. The source of the myristoleic acid was listed as Nu-Chek Prep., Inc. Nu-Chek Prep., Inc. presently lists myristoleic acid at $80 for one gram, $375 for 5 grams or, projected, about $75,000/kilo, an entirely non-economic price. For at least these reasons, up until now a 40% active liquid CMO has not been available while being eminently desirable.

Currently, there is no economical method for producing CMO in a liquid form at ambient-temperatures in commercial quantities.

BRIEF SUMMARY OF THE INVENTION

The method of the present invention provides an economical method for producing CMO in a liquid form at ambient-temperatures in commercial quantities.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein:

FIG. 1 shows the reaction of cetyl alcohol with myristoleic acid to yield cetyl myristoleate.

DETAILED DESCRIPTION OF THE INVENTION

Sources of Myristoleic Acid

Myristoleic acid occurs (as the triglyceride) naturally in significant amounts only in beef tallow and in one solitary vegetable butter.

Beef Tallow as a Source of Myristoleic Acid

Beef tallow can contain low levels (up to 2%) myristoleic acid (as the triglyceride). Within this constraint, the highest level, about 2%, occurs in so-called fleshing grease, which is tallow nearest the skin of the animal. Myristoleic acid is produced from tallow by a series of steps, beginning with fat splitting which breaks the triglyceride into its component fatty acids and glycerine. The fatty acids are then concentrated, in commercial practice, by a series of high-temperature, high-vacuum, fractional distillations. Commercial sales have been achieved with the end-result mixed fatty acids, mostly myristic and myristoleic.

The downstream cetyl esters are manufactured thereafter by reaction of these mixed fatty acids with cetyl alcohol.

Cetyl ester sales are to the dietary supplement industry and, so far, are relatively small, probably about 5 to 10 million dollars per year.

The commercial cetyl esters of mixed myristic/myristoleic acids, together, comprise a hard wax with a melting point of about 48° C. (~120° F.). It is noteworthy that this material cannot be injected directly into a softgel capsule.

Vegetable Butter Source of Myristoleic Acid

There is a tree occurring in nations of West Central Africa (for example, Ghana, Sierra Leone, and Angola) called, botanically, Pycnanthus Angolensis, and also, more commonly, Pycnanthus Kombo. The tree has nuts containing a seedfat, at about 50% by weight of the nut (commonly called kombo butter). This seedfat is the only significant vegetable source of myristoleic acid (again, as triglyceride).

The fatty acid profile of commercially available tallow-based myristoleic/myristic fatty acids is shown in Table 1.

TABLE 1

Fatty Acid Profile of Commercial Myristic
and Myristoleic Acids (Typical)

| Specific Fatty Acid (Fatty Acid Carbon Chain Length: Number of Double Bonds) | Percent of Specific Fatty Acid In Mixture |
|---|---|
| $<C_{14}$ | 1.3 |
| $C_{14:0}$ | 53.8 |
| $C_{14:1}$ | 40.6 |
| $C_{16:0}$ | 0.9 |
| $C_{17}$ | 0.8 |
| $C_{18:0}$ | 0.1 |
| $C_{18:1}$ | 2.5 |
| Others | 0.1 |

Cetyl myristoleate is made commercially by the esterification of these mixed fatty acids with cetyl alcohol. This has been done commercially in multi-ton quantities. The fatty acid profile of the esters, typically, is also as shown in Table 1.

By a series of steps (fat splitting, molecular distillation, and esterification) commercial tonnages of cetyl esters of mixed fatty acids derived from kombo butter have likewise been achieved. The fatty acid profile of this material is shown in Table 2.

TABLE 2

Fatty Acid Profile of Kombo
Butter-Based Cetyl Esters (Typical)

| Specific Fatty Acid (Fatty Acid Carbon Chain Length: Number of Double Bonds) | Percent of Specific Fatty Acid In Mixture |
|---|---|
| $<C_{14}$ | 6.6 |
| $C_{14:0}$ | 68.6 |
| $C_{14:1}$ | 15.1 |
| $C_{16:0}$ | 2.8 |
| $C_{16:1}$ | 1.9 |
| $C_{18:0}$ | 0.6 |
| $C_{18:1}$ | 3.6 |
| $>C_{18:1}$ | 0.8 |

This product is also a hard wax that melts at a slightly higher temperature than the analogous tallow-based cetyl myristoleate wax. The active ingredient, cetyl myristoleate, is only about 40% of its level in the tallow-based material. Importantly, the hard wax has a melting temperature that is too high melting to be injected directly into a softgel capsule.

"Soft Gel Capsules: An Elegant and Versatile Dosage Form", *Supplement Industry Executive* (6) describes the methods of in vivo delivery, the manufacturing process, and the basic formulations of softgel capsules as follows:

"Soft Gels (soft gelatin capsules) are becoming popular dosage forms for the administration of liquids, suspensions, pastes and dry powders in the dietary supplement industry. Soft gels have many advantages. These include, but are not limited to:

1. Ease of swallowing
2. The ability to mask unpleasant odors and tastes
3. The ability to have an elegant appearance with a wide choice of colors
4. Easily dissolvable in the digestive tract
5. Enhanced bio-availability of the active ingredient Manufacturing Process In the manufacturing process of making soft gel capsules, two gelatin ribbons pass between twin rotating die cylinders. As the ribbons meet, the liquid to be encapsulated is injected between them. The capsule halves are sealed and ejected by the continuous rotation of the cylinders. The shells containing the fill are then dried at room temperature so that the water content of each shell ranges from six to ten percent.

Basic Formulations

The formulation of capsule fill can be developed to fulfill the specifications and end-use requirements of the product. Capsulation of liquids that are immiscible with water and non-volatile, such as vegetable oils and vitamin E, are easy and require little or no formulation. However, solids that are not sufficiently soluble in liquids are capsulated as suspensions. Such materials should have a particle size of 80 mesh or finer.

Capsulation of suspensions is the most common form for a large group of dietary products. Suspension formulation requires a suspending agent to prevent the settling of the solids and to maintain homogeneity throughout capsulation. The most widely used suspending agent for oil-based formulation is wax (such as beeswax), and polyethylene glycols in a non-oil-base.

Powdered extracts are usually combined with soybean oil (as a carrier), yellow beeswax (as a suspension and thickening agent), and lecithin (as a lubricant) for formulation in softgels. The relative amounts of the extract and the other ingredients depend upon the desired extract dose to be administered."

CMO Softgel Encapsulation

Currently, both forms of cetyl myristoleate, that based on tallow fatty acids and that based on kombo butter, have melting points too high for the liquidity needed for the encapsulation injection described above. In practice the cetyl myristoleate must be blended with an edible oil or put into an inert carrier such as cornstarch before the CMO can be encapsulated. For combination with an edible oil, the CMO can be blended at an approximately 70/30 CMO/oil level ratio. When combined with an inert carrier such as cornstarch, the CMO can be combined at an approximately 50/50 balance in a liquid suspension. The CMO powder is made by combining the CMO hard wax with cornstarch in a 50/50 ratio. This CMO-cornstarch powder is then combined with a suspending liquid in a 50/50 ratio to make a liquid suspension. The problem that results from the need to blend the CMO with an edible oil or inert carrier is that less CMO is able to be put in the capsule. Therefore, there is less amount of the active ingredient in the capsule and more capsules have to be taken to achieve an effective daily dose.

Table 3 illustrates how CMO (with 40% $C_{14:1}$) that is liquid at room temperature diminishes the number of capsules required to achieve an effective daily dose. By using the method of the present invention, commercial quantities of CMO that are liquid at room temperature can be produced, thereby creating softgel capsules with more active $C_{14:1}$ ingredient per capsule.

TABLE 3

Effective Dosages for CMO (Typical)

| Formulation | Active Ingredient[1] Mg/Capsule | Inerts[2] Mg/Capsule | Capsules/Day |
|---|---|---|---|
| Neat[3] | 560 | 240 | 2.7 |
| CMO/Oil 70/30 | 392 | 408 | 3.8 |
| CMO/Cornstarch 50/50 Suspension of a 50/50 powder | 200 | 600 | 7.5 |

[1]Based on 70% of 800 mg capacity/capsule
[2]Non-active components in capsule
[3]A 40% $C_{14:1}$ liquid CMO Table 3 is based on the following calculations. For these examples, an effective dose of CMO is approximately 1500 mg/day of $C_{14:1}$. However, effective doses of CMO can range from about 400 mg/day to about 1500 mg/day. A dose range of 900 mg/day-1200 mg/day is common. The effective dose for an individual will vary greatly depending on various factors, including, but not limited to, the individual's body weight.

Based on typical fatty acid profiles, the cetyl ester complex contains 40% cetyl myristoleate. In these examples, CMO is 70% of the formulation and the maximum weight capacity in the softgel is 800 mg.

The liquid CMO prepared using the method of the present invention contains approximately 40% $C_{14:1}$ per capsule. The weight capacity of the softgel is 800 mg. 70% of the softgel contents is CMO. Therefore 70% of 800 mg/capsule=0.70*800 mg/capsule=560 mg/capsule. If the effective dose is 1500 mg/day, then 2.7 capsules per day would be required to achieve the effective dose.

Currently, the commercially available CMO that is mixed with an edible oil is 70 parts CMO and 30 parts edible oil. 70% of the softgel contents is the CMO/oil mixture, of which only 70% is CMO. Therefore, 70% of 70% is 0.70*0.70=0.49% of the capsule is CMO. Since the capsule is 800 mg, the percentage of CMO in the capsules that are commercially available are 0.49%*800 mg/capsule=392 mg/capsule. Therefore, to achieve an effective dose of 1500 mg/day, 3.8 capsules are needed.

CMO is also currently available as a 50/50 suspension of a 50/50 powder of CMO on cornstarch. Since 50% of the softgel contents is the CMO/50/50 cornstarch mixture, and only 50% of that is CMO, the total amount of CMO in this type of capsule is 800 mg/capsule (0.50)*(0.50)=200 mg. Therefore, 7.5 capsules per day are needed to achieve the 1500 mg/day effective dose of CMO.

Therefore, there are distinct advantages for the availability of liquid-at-ambient-temperature CMO in commercial quantities provided by the instant invention; 1) the method of encapsulating a liquid is easier, 2) higher levels of the active, effective ingredient per capsule than is currently available can be achieved, and 3) because of the higher level of active ingredient per capsule, less capsules are required to achieve an effective dosage.

Method to Prepare Liquid Cetyl Esters with 40% Active Ingredient (CMO).

The present invention provides a method for the manufacture of a complex of cetyl esters of straight-chain fatty acids that is liquid below about 100° F. in commercial quantities, with a minimum of 40% cetyl myristoleate and the balance a mixture of cetyl oleate, cetyl myristate and smaller amounts of cetyl esters of lauric acid, palmitic acid, palmitoleate acid, stearic acid and linoleic acid. Because this complex of fatty acids will be liquid below about 100° F., this method provides for commercial quantities of CMO that can be directly encapsulated in softgel capsules. The practical effect is to diminish the number of capsules needed per day to achieve an effective dose and to diminish the amount of inert, non-active and non-effective ingredients in the dosage.

EXAMPLE 1

A Multi-Step Process to Prepare Liquid Cetyl Esters with 40% Active Ingredient (Cetyl Myristoleate)

Step 1—Separation of Unsaturated and Saturated Fatty Acids

The first step comprises mixing fatty acids containing myristic and myristoleic acid with methanol with gentle heating, up to 150° F. for 10-40 minutes. Methanol is not the only alcohol that can be used in this step. Any aliphatic alcohol six carbons or shorter will work. Methanol is the preferred alcohol as it is the most economical and the easiest to strip away. The myristoleic acid ($C_{14:1}$) content of the starting fatty acid mixture can range from about 2% to about 50%. The ratio of mixing the starting fatty acids with the methanol ranges from about 125 g fatty acids/1500 mg methanol on the dilute side to about 550 g fatty acids/1500 g methanol on the concentrated side. Too concentrated a solution makes filtration difficult and too dilute a solution involves uneconomic amounts of methanol.

A commercial fatty acid mixture with the typical carbon chain length profile shown in Table 1 was purchased from Cognis Corporation, Cincinnati, Ohio. Cognis Corporation's commercially available fatty acids contain about 35% to about 42% myristoleic ($C_{14:1}$). In a stirred reaction vessel, 379 g of commercial fatty acids comprised of about 94% total myristic ($C_{14:0}$) and myristoleic ($C_{14:1}$) acid was mixed with gentle heating with about 1500 g of methanol. At about 50° C., solution of the solid fatty acids was complete.

The solution of fatty acids in methanol was adjusted to a temperature of 20° F. by external cooling and held at that temperature, with stirring, for about one hour until solid crystals (a solid cake), made up largely of the saturated $C_{14:0}$ fatty acids (myristic), was completely formed. The temperature can be adjusted from about 15° F. to about 30° F. The solid cake was separated by filtration or centrifugation. The filtrate consisting of methanol and myristoleic-rich fatty acids was isolated and the methanol stripped away. The yield of dry cake was about 46% of the starting commercial fatty acids and the myristoleic-rich fraction isolated from the filtrate was about 50%. The cake had a melting point higher than the starting fatty acids and was not used further. It contains 80-90% myristic acid ($C_{14:0}$).

The fatty acids from the stripped filtrate are liquid at ambient (room) temperature (approximately 80° F.-85° F.) and have the analysis shown in Table 4 below:

TABLE 4

High Myristoleic Acid Mixture
(fatty acids from the stripped filtrate)

| Fatty Acid | % in Filtrate |
|---|---|
| <$C_{14}$ | 6.2 |
| $C_{14:0}$ (myristic) | 16.4 |

TABLE 4-continued

High Myristoleic Acid Mixture
(fatty acids from the stripped filtrate)

| Fatty Acid | % in Filtrate |
|---|---|
| $C_{14:1}$ (myristoleic) | 68.4 |
| Others | 9.0 |

These liquid fatty acids can be esterified with cetyl alcohol to yield mixed cetyl esters containing the same level of myristic acid ($C_{14:1}$) [as the cetyl esters]. This gives a very rich (with respect to $C_{14:1}$ content) and potent formulation. For example, Table 4 shows a 68.4% myristoleic ($C_{14:1}$) product. Esterification of this material with cetyl alcohol yields a liquid end product cetyl myristoleate with 68.4% $C_{14:1}$ as cetyl ester. This product is liquid at ambient temperature and is very rich in $C_{14:1}$. Such a formulation is within the scope of this invention.

The subsequent step (step 2) to dilute the $C_{14:1}$ content (at 68.4% after the separation of saturated and unsaturated fatty acids) with the addition of oleic acid (high $C_{18:1}$) acid (or other liquid fatty acids) is also within the scope of the invention. Dilution yields a more economical product. Cetyl esters that are liquid at ambient (80° F.-85° F.) temperature ranging from about 22% $C_{14:1}$ to about 80% $C_{14:1}$ are all within the scope of this invention. Currently, the preferred percentage of $C_{14:1}$ in the liquid end product cetyl esters is 40%.

Liquid fatty acids ranging from about 20% $C_{14:1}$ to about 80% $C_{14:1}$ are within the scope of this invention. The derived cetyl esters with the same range (20%-80%) of $C_{14:1}$ content likewise are within the scope of this invention.

Fatty acids obtained from a vegetable source, such as kombo butter, are also within the scope of this invention. Crude kombo butter can be used as well as refined, bleached or deodorized kombo butter. In addition, any combination of refined, bleached, deodorized or crude kombo butter is also within the scope of the invention. Because the fatty acid profile of vegetable-sourced fatty acids has a lower $C_{14:1}$ content than tallow-sourced fatty acids, separation of the mixture of unsaturated and saturated fatty acids needs to be repeated until the soft fatty acids are at the level of about 60% or greater $C_{14:1}$ content. This separation can be achieved using the same method described in Step 1 above; namely combining the vegetable sourced fatty acids containing myristic and myristoleic acid with methanol or any aliphatic alcohol six carbons or shorter, mixing with gentle heating until sold crystals form, separating the solid crystals by, for example but not limited to filtration or centrifugation.

Step 2—Dilution with Low-Titer Oleic Acid

The second step comprises diluting myristoleic-rich liquid fatty acids prepared as in Step 1 (as methanol-stripped filtrate) with a low-titer fatty acid. Many low-titer fatty acids can be used. Examples include, but are not limited to, liquid fatty acids derived (by fat splitting) from soybean oil, sunflowerseed oil, canola oil, palm olein (the "soft" fraction of palm oil) and olive oil. Other, less-common, room temperature-liquid fatty acids are also within the scope of this invention and can serve as the diluent that reduces the percentage of $C_{14:1}$ fatty acids.

For example, the 68% myristoleic acid mixture shown in Table 4 can be diluted with oleic acid to yield the 40% $C_{14:1}$ liquid fatty acid shown in Table 6. There are various grades of oleic acids (and other fatty acids), all of which can be used in this step. Low-titer oleic acid is available commercially from several sources. One example is Cognis Corporation. However, any source of low-titer oleic acid (or other fatty acid) can be used in the method of this invention. Currently, commercially available oleic acids contain in excess of 70% $C_{18:1}$ (oleic acid).

The typical fatty acid profile of commercial low-titer oleic acid is shown in Table 5.

TABLE 5

Commercial Low-Titer Oleic Acid

| Fatty Acid | Typical Percentage |
|---|---|
| $C_{14:0}$ (myristic) | 2 |
| $C_{16:0}$ (palmitic) | 4 |
| $C_{16:1}$ (palmitoleic) | 6 |
| $C_{18:0}$ (stearic) | 1 |
| $C_{18:1}$ (oleic) | 72 |
| $C_{18:2}$ (linoleic) | 9 |
| Others | 6 |

Four hundred grams (400 g) of myristoleic-rich liquid fatty acids prepared in Step 1 (as methanol-stripped filtrate) were diluted to 685 g with 285 g of low-titer oleic acid. The fatty acid profile of the mixed fatty acids, which are liquid at room temperature (~75° F.), is shown in Table 6.

TABLE 6

Properties of 40% $C_{14:1}$ Liquid Fatty Acids

| Fatty Acid | Percent in Diluted Sample |
|---|---|
| $C_{12:0}$ (lauric) | 2.4 |
| $C_{14:0}$ (myristic) | 9.7 |
| $C_{14:1}$ (myristoleic) | 40.0 |
| $C_{16:0}$ (palmitic) | 3.0 |
| $C_{16:1}$ (palmitoleic) | 1.5 |
| $C_{18:0}$ (stearic) | 0.8 |
| $C_{18:1}$ (oleic) | 36.6 |
| $C_{18:2}$ (linoleic) | 6.0 |

In these examples, the dilution with oleic acid was chosen on the basis of oleic acid's easy availability, good economics, and compatibility with the other fatty acid components in the Cognis precursor fatty acids. This is not meant to be limiting. Tables 7, 8, 9, 10, and 11 show other possibilities for the diluting fatty acids. Tables 7-11 show liquid fatty acids derived (by fat splitting and distillation) from soybean oil, sunflowerseed oil, canola oil, palm olein (the "soft" fraction of palm oil) and olive oil. All of these fatty acids, and other, less-common, room temperature-liquid fatty acids are within the scope of this invention and serve, like low-titer oleic acid, as the diluent that reduces $C_{14:1}$ fatty acids at the 70% $C_{14:1}$ level that leads, as one example, to the commercial product (as cetyl ester) at 40% $C_{14:1}$.

TABLE 7

Fatty Acid Profile of Soy Fatty Acids

| Fatty Acid | Typical % of Each Fatty Acid |
|---|---|
| $C_{16:0}$ (palmitic) | 11.0 |
| $C_{18:0}$ (stearic) | 4.0 |
| $C_{18:1}$ (oleic) | 21.0 |
| $C_{18:2}$ (linoleic) | 55.5 |
| $C_{18:3}$ (linolenic) | 8.5 |

TABLE 8

Fatty Acid Profile of Sunflowerseed Oil-Based Fatty Acids

| Fatty Acid | Typical % of Each Fatty Acid |
|---|---|
| $C_{14:0}$ (myristic) | 0.5 |
| $C_{16:0}$ (palmitic) | 6.5 |
| $C_{18:0}$ (stearic) | 4.0 |
| $C_{18:1}$ (oleic) | 17.0 |
| $C_{18:2}$ (linoleic) | 72.5 |

TABLE 9

Fatty Acid Profile of Canola Oil-Based Fatty Acids

| Fatty Acid | Typical % of Each Fatty Acid |
|---|---|
| $C_{16:0}$ (palmitic) | 4.0 |
| $C_{18:0}$ (stearic) | — |
| $C_{18:1}$ (oleic) | 56.0 |
| $C_{18:2}$ (linoleic) | 26.0 |
| $C_{18:3}$ (linolenic) | 10.0 |
| Others | 4.0 |

TABLE 10

Fatty Acid Profile of Palm Olein-Based Fatty Acids

| Fatty Acid | Typical % of Each Fatty Acid |
|---|---|
| $C_{16:0}$ (palmitic) | 40 |
| $C_{18:0}$ (stearic) | 5 |
| $C_{18:1}$ (oleic) | 44 |
| $C_{18:2}$ (linoleic) | 10 |
| Others | 1 |

TABLE 11

Fatty Acid Profile of Olive Oil-Based Fatty Acids

| Fatty Acid | Typical % of Each Fatty Acid |
|---|---|
| $C_{16:0}$ (palmitic) | 13.0 |
| $C_{16:1}$ (palmitoleic) | 1.0 |
| $C_{18:0}$ (stearic) | 2.5 |
| $C_{18:1}$ (oleic) | 74.0 |
| $C_{18:2}$ (linoleic) | 9.0 |

Step 3—Esterification of Room-Temperature-Liquid Fatty Acids with Cetyl Alcohol

The third step comprises esterification of the room-temperature liquid fatty acids with cetyl alcohol to yield cetyl myristoleate. A ratio of 1.06 gram mol cetyl alcohol to 1.0 gram mol of fatty acids is used. This ratio is important since it is near stoichiometry (exact molar equivalency) with a little (0.06 gram mol) excess of the cetyl alcohol to ensure that all of the fatty acids are used up in the reaction. This ratio can range from about 0.94-1.14/1 gram mol cetyl alcohol to gram mol fatty acids. Using a ratio somewhat outside this range yielding a product that is liquid is also within the scope of the invention. However, straying substantially from this ratio will yield cetyl esters with excess acids or excess alcohol which is undesirable from a purity standpoint.

In this example, 251 g (1 gram mol) of the mixed liquid fatty acids shown in Table 6 is mixed with 271 g (1.06 gram mol) of cetyl alcohol (commercially available from Kao Corporation and Procter and Gamble, among others) along with 2 g of hypophosphorus acid as a catalyst (50/50 in water). Hypophosphorus acid (50/50 in water) is available commercially from J. T. Baker, among others. The mixture is heated with stirring with a nitrogen sparge and an arrangement to facilitate the removal of the water formed as a by-product of the reaction (about 18 grams). The reaction mixture is heated to 195-205° C. and held at that temperature until virtually all of the water in the reaction is removed and the acid value drops below 10. At that point the hydroxyl value is less than 20. The reaction is stopped, cooled to room temperature and the product discharged into a glass container. Theoretical yield is approximately 500 g of liquid cetyl esters of mixed fatty acids with the fatty acid profile shown in Table 6. Melting point is about 80° F.

The results of these 3 invention steps, 1) separation of unsaturated and saturated fatty acids, 2) dilution with low-titer oleic (or other) liquid fatty acid, and 3) esterification of ambient-temperature liquid fatty acids with cetyl alcohol provides an economical method for producing CMO in a liquid form at ambient temperatures in commercial quantities.

REFERENCES (1) H. W. Diehl & E. L. May, "Cetyl Myristoleate Isolated From Swiss Albino Mice; An Apparent Protective Agent Against Adjuvant Arthritis In Rats", *J. Pharm. Sci* (1994); 83: 296-9.
(2) Kenneth W. Hunter, Jr., Ruth A. Gault, Jeffrey S. Stehouwer, and Suk-Wah Tam-Chang, "Synthesis Of Cetyl Myristoleate And Evaluation Of Its Therapeutic Efficacy In A Murine Model Of Collagen-Induced Arthritis", *Pharmacological Research,* 47 (2003) 43-47.
(3) U.S. Pat. No. 4,049,824 to Harry Diehl, "Cetyl Myristoleate ", Sep. 20, 1977.
(4) U.S. Pat. No. 4,113,881 to Harry Diehl, "A Method Of Treating Rheumatoid Arthritis", Sep. 12, 1978.
(5) U.S. Pat. No. 5,569,676 to Harry Diehl, "A Method for the Treatment of Osteoarthritis", Oct. 29, 1996.
(6) "Soft Gel Capsules: An Elegant and Versatile Dosage Form", Supplement Industry Executive.

The foregoing embodiments are presented by way of example only; the scope of the present invention is to be limited only by the following claims.

What is claimed is:

1. A method of preparing ambient-temperature liquid cetyl esters having a range of about 40% cetyl myristoleate to about 80% cetyl myristoleate, said method comprising the steps of:
   1) separation of a starting solid mixture of unsaturated and saturated fatty acids into a solid saturated fatty acid component and a purified liquid unsaturated fatty acid component, wherein the content of said starting solid mixture of unsaturated and saturated fatty acids is a range of about 2 to 50% myristoleic acid;
   2) dilution of said purified liquid unsaturated fatty acid component by mixing said liquid unsaturated fatty acids with a specified amount of liquid room temperature-fatty acids selected from the group consisting of oleic acid fatty acids, soybean oil fatty acids, sunflower seed oil fatty acids, canola oil fatty acids, palm olein fatty acids, and olive oil fatty acids; and
   3) esterification of the diluted product of step 2), comprising mixing said diluted liquid unsaturated fatty acids with cetyl alcohol;
      wherein said separation, dilution and esterification steps are economically suitable for commercial application; and wherein said mixture of saturated and unsaturated fatty acids of step 1) is obtained from a source selected from the group consisting of beef tallow and kombo butter.

2. The method of claim 1, wherein said separation of unsaturated and saturated fatty acids comprises:
 a) heating said mixture of unsaturated and saturated fatty acids with an aliphatic alcohol six carbons or shorter until solution of the solid fatty acids,
 b) adjusting the temperature to from about 15° F. to about 30° F. until solid crystals are formed into a solid cake, and
 c) separating the solid cake.

3. The method of claim 2, wherein said aliphatic alcohol is methanol.

4. The method of claim 2, wherein said adjusting the temperature to from about 15° F. to about 30° F. is to about 20° F.

5. The method of claim 2, wherein said aliphatic alcohol six carbons or shorter is present at a ratio of from about 125 g fatty acids/1500 mg aliphatic alcohol to about 550 g fatty acids/1500 g aliphatic alcohol.

6. The method of claim 3, wherein said heating said mixture of unsaturated and saturated fatty acids comprises mixing said mixture of unsaturated and saturated fatty acids with said methanol at a ratio of from about 125 g fatty acids/1500 mg methanol to about 550 g fatty acids/1500 g methanol.

7. The method of claim 2, wherein said separation of solid cake is achieved by filtration.

8. The method of claim 2, wherein said separation of solid cake is achieved by centrifugation.

9. The method of claim 1, wherein said range of about 40% cetyl myristoleate to about 80% cetyl myristoleate is about 40% cetyl myristoleate.

10. The method of claim 1, wherein said dilution of said specified amount of room temperature-liquid fatty acids is oleic acid.

11. The method of claim 1, wherein said esterification comprises mixing said diluted unsaturated fatty acids with cetyl alcohol at a ratio of about 1.06 gram mol cetyl alcohol to about 1.00 gram mol acids.

12. The method of claim 1, wherein said esterification comprises mixing said diluted unsaturated fatty acids with cetyl alcohol at near stoichiometry with a small excess of said cetyl alcohol.

13. The method of claim 1, wherein said saturated and unsaturated fatty acid source is kombo butter.

14. The method of claim 1, wherein said separation of a mixture of unsaturated and saturated fatty acids is repeated until soft fatty acids at the level of about 60% or greater $C_{14:1}$ is achieved.

15. The method of claim 13, wherein said kombo butter is selected from the group consisting of crude kombo butter, refined kombo butter, bleached kombo butter, and deodorized kombo butter.

16. The method of claim 13, wherein said kombo butter is a mixture comprised of any combination of crude, refined, bleached and deodorized kombo butter.

17. The method of claim 1, wherein said ambient temperature is from about 80° F. to about 85° F.

\* \* \* \* \*